(12) United States Patent
Gupta

(10) Patent No.: US 7,179,477 B2
(45) Date of Patent: Feb. 20, 2007

(54) COSMETIC DERMABRASION TREATMENT SYSTEM

(76) Inventor: Shyam K Gupta, Bioderm Research, 5221 E. Windrose Dr., Scottsdale, AZ (US) 85254

( * ) Notice: Subject to any disclaimer, the term of this patent is extended or adjusted under 35 U.S.C. 154(b) by 712 days.

(21) Appl. No.: 10/604,781

(22) Filed: Aug. 15, 2003

(65) Prior Publication Data

US 2005/0037038 A1    Feb. 17, 2005

(51) Int. Cl.
*A61K 8/00* (2006.01)
*A61K 8/02* (2006.01)
*A61K 8/04* (2006.01)

(52) U.S. Cl. ....................... 424/401; 424/400
(58) Field of Classification Search ................ 424/400, 424/401
See application file for complete search history.

(56) References Cited

U.S. PATENT DOCUMENTS 4,536,405 A * 8/1985 Nara et al. ................... 514/781
5,824,666 A * 10/1998 Deckner et al. ............. 514/152

* cited by examiner

*Primary Examiner*—Shelley A. Dodson

(57) ABSTRACT

The present invention provides a complementary three-step dermabrasion system that provides treatment for skin conditions such as acne scars, wound scars, and other visually unappealing skin disfigurements, which constitutes the following, (1) Dermal Resurfacing with an adhesive composition, (2) Dermal Polishing with a polishing composition, and (3) Dermal Regeneration with a collagen-building and cell-proliferative composition.

12 Claims, No Drawings

COSMETIC DERMABRASION TREATMENT SYSTEM

BACKGROUND OF INVENTION

Dermabrasion generally consists of removing the epidermis and superficial layers of the dermis. Dermabrasion can be used as a therapeutic process for several skin conditions. In particular, indications for dermabrasion include acne scarring, active acne, nasal rhinophyma, traumatic or surgical scarring, tattoos, lentigenes, facial rhytids, keratoses, and more recently, wrinkles caused by natural aging. This has been additionally discussed in U.S. patent application 20030113540 (Anderson et al.).

Resurfacing the human skin can be achieved by several mechanisms that are aimed primarily at disrupting the epidermal and upper dermal layers. Human skin is composed of at least three layers of variable thickness, depending upon body location. The uppermost layer, or epidermis, is usually as thin as a sheet of paper. The layer just below the epidermis is the dermis, which is largely composed of collagen and makes up the "leather" layer of the skin. The dermis may vary in thickness from that of paper to as thick as half an inch on the neck and back. The layer below the dermis may be composed of either muscle (around the eyes and mouth) or fat, otherwise known as subcutaneous fat. New human surface skin is regenerated following resurfacing by the surrounding islands of normal epidermis and epidermal cells migrating from the deep hair pores and other pore structures that permeate the upper dermis, mid dermis, and epidermis. If excessive scar tissue, rather than a plethora of epidermal cells, closes a surface wound, then an unsightly scar will result. The key to all resurfacing procedures is a controlled destruction of the desired area that still allows the regeneration of new tissues from pores and neighboring islands of untouched, untreated skin.

The procedures currently used in human skin resurfacing include chemical peeling, dermabrasion, laser surgery, and most recently the "power peel" or crystalline peel. In chemical peeling, a caustic, disruptive or destructive liquid agent is applied to the surface skin to damage existing epidermal and dermal cells, which will then be replaced by the body. Peeling agents act depending on their strength and type. Examples of chemical peeling agents include fruit acid peel, glycolic acid peel, and trichloracetic acid (TCA) and phenol peels. TCA peels can be made to act at deeper and varying depths by varying the concentration of TCA used to destroy the surface skin. Concentrations as low as 5–10% TCA will behave similarly to a fruit acid peel, and concentrations of 50% TCA may cause severe peeling burns, which simulates phenol, and may border on scarring. Phenol, when diluted with water, penetrates more deeply and destroys more tissue than most other peeling agents.

Dermabrasion literally means abrasion of the skin and is a procedure in which a rotating sanding wheel, or abrasive substance, is applied to a rigidified skin to sand out an undesirable feature, mark, or scar. Some high-speed dermabrasion rotors go up to 200,000 revolutions per minute (rpm) and do not require any rigidity to the tissues; however, they require extremely skilled personnel and special instrumentation and are impractical for most home use. A minor mistake with such a high powered machine can have disastrous results. Dermabrasion is usually performed with a rotating wheel operating at speeds under 10,000 rpm after the skin has been rigidified using Freon or dichlorotetrafluoroethane. In dermabrasion (unlike laser surgery), the person operating the abrading wheel has a direct tactile sense of pressing the wheel into the tissues being treated and can apply differential pressure to areas of elevation. Dermabrasion can be achieved to various depths depending upon the depth of freezing (rigidification), the number of passes of the abrader, the type of abrasive wheel, and the pressure applied. This procedure is waning in use, however, due to the unavailability of Freon.

Presently, dermabrasion is carried out by utilizing powered air-driven units. Such units include a tip that rotates at high speed, for example, 600 to 35,000 RPM. The tip receives a sanding bit, which is rotated by the tip while it is pressed against the dermis of a patient. In this way, the epidermal layer of skin may be removed, which effects removal of superficial scars of the skin and improvement in appearance of intermediate depth scars. Following dermabrasion, a new layer of epidermis forms at a depth lower than that of the original epidermis. Dermabrasion may be carried out several times to treat deep scarring of the skin. Despite the efficacy of utilizing powerful airdriven units according to the prior art, such units have several drawbacks. For example, such units are both costly and relatively complex and impractical for home use by consumer. This has been further discussed in U.S. Pat. No. 5,800,446 (Banuchi). Several other machines and apparatus have recently been devised for dermabrasion, for example U.S. Patent Applications 20030130628 (Duffy), 20030125660 (Moutafis et al.), 20030097139 (Karasiuk), 20030093089 (Greenberg), 20020169461 (Simon et al.), 20020133176 (Parkin et al.), 20020128663 (Mercier et al.), 20020107529 (Bernabei), 20020040199 (Klopotek), 20020016601 (Shadduk), 20020107527 (Burres) 20010034519 (Goble et al.), 20010023327 (Hill), and 20010049511 (Coleman et al.). These all are also very complex and not useful for in-home application by consumer.

In a new technique referred to as crystal microdermabrasion, aluminum oxide (corundum) crystals flowing in an air stream have been applied to the skin. In this technique, there is less bleeding, fewer complications, better compliance, and no need for local anesthesia or high surgical skills. In the microdermabrasion technique, the velocity and density of crystals within the stream of air is related to the degree of abrasion which can occur over a fixed period of time. In the past, the crystal velocity has been controlled primarily by providing a bleed valve for the introduction of additional air into the stream of air. In a suction system this tends to slow the velocity of the operative air stream and thereby reduce the degree of abrasion. U.S. Pat. No. 6,592,595 (Mallet et al.) describes these techniques in further detail. Again, such units are costly and relatively complex. U.S. Patent Application 20020090385 (Fox et al.) discloses microdermabrasion with a crystalline emulsion. The crystalline emulsion includes a mixture of coated crystals and a carrier. The coated crystals are formed by combining magnesium oxide, aluminum oxide or a combination of the two with methicone, adding a catalyst, such as ammonia, and mixing, then baking the resulting slurry mixture until the mixture is dry. The coated crystals are able to stay in the emulsion in a carrier.

The power peel is relatively new in the United States and is basically a method of "sandblasting" the skin. This procedure has been touted to reduce acne scars and remove all other types of scars and imperfections. The power peel is a process by which aluminum oxide crystals, which are extremely hard, are shot at the skin with 25 psi of air pressure. Safe operation of these devices requires the use of a limited number of passes or accurate control of pass speed to the target area. A power peel that only removes the epidermis of the skin will not result in any alteration of scar formation and produces very little long-lasting cosmetic effect. However, aluminum oxide crystals that are shot deeply enough into the skin to remove or alter deeper structures such as scars or pits can cause granuloma formation or foreign body reaction because aluminum oxide crystals are not biocompatible. Thus the body extrudes or encapsulates unwanted particles at levels of skin where protection is necessary, which may lead to disease and unsightly scarring. Even systems that include a vacuum apparatus to suck away unwanted particles do not remove 100% of the particles. Even a small amount of residue crystals can lead to disease and other cellular difficulties. U.S. Pat. No. 6,306,119 (Weber et al.) further discusses this topic. Another variant of this methodology, i.e. the use of solid particles such as sand, alumina, or hard fibers, etc. is disclosed in U.S. Pat. No. 6,017,351 (Street) in which a cosmetic pad for use in removing surface detritus from the skin at pressures a lay person can apply in scrubbing the skin is comprised of a segment of lofty, fibrous, non-woven structure of mixed denier organic (e.g., nylon or polyester) crimped filaments bonded at contacting points with a binder such as thermosetting resin and containing finely divided, biocompatible, soft abrasive particles. This is essentially equivalent to the use of sand paper or emery cloth for dermabrasion. This method does not permit dermabrasion to any precise depth and can be painful.

Another dermabrasion technique is generally known as "tape stripping" and involves adhering a tape having a pressure-sensitive adhesive backing to the user's body and then pulling the tape off the body part to remove an outer layer of skin. Of particular note is U.S. Pat. No. 5,720,963 wherein Smith teaches a variety of long term skin treatments, several of which include a regime of five to ten tape stripping steps repeated twice daily in order to chronically disrupt a skin water barrier. Smith also teaches that more severe treatments can be carried out less frequently (e.g., every second or third day) by using a more aggressive skin-adhering adhesive, such as a cyanoacrylate adhesive. Although he discloses several different tape stripping approaches in U.S. Pat. No. 5,720,963, Smith states that his tape stripping method has numerous draw-backs, which include a wide range of response of various individuals to tape stripping, as well as a stated need for an expensive laboratory instrument to monitor the process. Moreover, Smith's teaching is directed entirely towards treatments extending over several months before obtaining discernible results. U.S. Pat. No. 6,290,659 (Hill) discloses yet another method of practicing the skin exfoliation comprises the steps of: 1) preparing a transparent exfoliation sheet having an adhesive-covered portion comparable in size and shape to a portion of the user's body that is to be exfoliated and attaching a handle along one edge of the sheet; 2) adhering that portion of the exfoliation sheet immediately adjacent the handle to a first edge of the predetermined portion of the body; 3) rubbing or pressing on the exfoliation sheet by moving one's hand or fingers from a staring position adjacent the handle toward that edge of the exfoliation sheet distal from the handle so as to attach substantially the entire sheet to the predetermined portion of the body by means of the pressure sensitive adhesive; 4) grasping the handle and pulling it along the surface of the predetermined portion of the body so as to separate the first exfoliation sheet from the portion of the body being exfoliated; 5) visually examining the removed first transparent exfoliation sheet to determine the amount of skin exfoliated; 6) preparing a new exfoliation sheet and repeating steps 1) through 5) until the amount of exfoliated skin noted at an ending repetition is discernibly less than the amount of exfoliated skin retained on the respective exfoliation sheet employed in the immediately preceding repetition. None of these "skin stripping" methods provide a complete solution to excess skin removal and rebuilding of normal skin surface.

Dermal scratching is another method practiced for dermabrasion, as disclosed in U.S. Pat. No. 5,454,384 and U.S. Pat. No. 5,012,797 (McAllister) wherein a target line or wrinkle is selected that the patient wishes to minimize or eradicate. A pair of lines is scratched in the skin parallel to and one on each side of the target line. Preferably two series of lines are then scratched in the skin, one series parallel to each of the first pair of lines, with a separation of at least 1/16 inch. The post-treatment steps include cleaning the scratches with antibacterial soap, drying the area, and massaging with antibacterial topical cream. Once the lines scratched in the skin are permitted to heal, the skin is found to be tightened. This method is suitable for application by a surgeon or dermatologist and not convenient for in-home use by consumer.

Laser surgery has recently become popular to remove or reduce wrinkles, remove tumors, and alter scars, although results are mixed. Several types of lasers are used, including carbon dioxide and erbium-YAG lasers. Carbon dioxide lasers deliver light radiation at a frequency that can vaporize and destroy surface skin. These lasers may be set on various pulse patterns to deliver precise and controlled amounts of laser radiation to the skin in a relatively uniform and homogenous fashion across the surface. An unfortunate disadvantage of this laser is that heat can be transmitted to the surrounding tissues. Additionally, after the first pass of the carbon dioxide laser, the skin begins to ooze and become wet at the surface as fluids build up in response to the damage. Since water and blood absorb in the infrared region, a second pass of the laser will penetrate to a variable depth, depending on how much surface ooze there is in the area. The ooze prevents the laser energy from reaching the target tissues uniformly. During laser irradiation, the tissues may begin to desiccate, which ultimately results in severe thermal damage. Depositing too much laser energy on the target tissues can result in persistent redness, scarring, and other complications or damage, even with thermal relaxation techniques to mitigate heat transfer. U.S. Pat. No. 6,077,294 (Cho et al.) discloses a method for the treatment of wrinkles on human skin, by stimulating collagen growth beneath the epidermis layer, comprising the steps of: arranging a pulsed dye laser generator in light communication with a pulsed dye laser delivery device. Laser methods require the services of a plastic surgeon or dermatologist and are expensive and not convenient.

After dermabrasion the rebuilding of skin requires recollagenation. Disfiguring cutaneous irregularities, such as acne scars, wrinkles, and post traumatic depressions are a consequence of the loss of collagen that supplies the tissue thickness and maintains an even surface contour. Re-collagenation is the rebuilding of this lost collagen. Materials that have been used clinically to replace the lost tissue volume by subcutaneous injection include liquid silicone, fat, paraffin, liquid bovine collagen, and other fibrin compounds. Collagen suspensions, such as the liquid bovine collagen disclosed in U.S. Pat. No. 4,424,208 (Wallace et al.), U.S. Pat. No. 4,582,640 (Smestad et al.), and U.S. Pat. No. 4,642,117 (Nguyen et al.) are problematic in that they routinely fail to add endogenous collagen to tissue. Over time, the liquid disperses between cells allowing intercellular collagenase to digest the collagen substrate. Fat transferred from other areas is lumpy and has an unpredictable pattern of reabsorption. More resilient materials like silicone are gradually excreted into neighboring tissues from the depressed areas as the scar tightens again. Substances like paraffin can initiate an inflammatory response that causes further collagen loss. These filling techniques, in which liquid materials are injected through a needle into the scar, are disadvantageous because an injectable substance does not create a space between the layers of tissue in the recipient scar bed and therefore does not initiate new collagen deposition. U.S. Pat. No. 5,397,352 (Burres) discloses a surgical method for implanting cadaver collagen for the restoration of lesions caused by the loss of collagen. The skin is perforated and a pocket is created under the skin. Human cadaver collagen is then introduced into the pocket and the skin perforation is closed. Over the next several months, the cadaver collagen is replaced by endogenous collagen. U.S. Pat. Nos. 4,061,731 and 4,006,220 (Gottlieb) discloses the use of fibrin stabilizer and plasma for collagen rebuilding, wherein said fibrin stabilizer is present in an amount effective to maintain fibrin within a cavity preferably formed under said scar. One fibrin stabilizer used is finely-divided collagen. The compositions promote the build-up of new collagen within the aforementioned cavity.

The above prior art citations clearly establish that dermabrasion has distinct advantages in treating skin conditions such as acne scars, wound scars, disfigurements of skin from diseases such as small pox, and other skin disfigurements. It is also clear from the above prior art citations that it would be advantageous to develop a procedure that can remove scars, wrinkles, and various other imperfections or lesions on the skin without introducing foreign bodies or substances that can cause adverse physiological reactions or produce unwanted physical or thermal damage or discomfort.

It is also clear from the above prior art citations that treatment of such skin disfigurement conditions ideally requires the following three steps, (1) removal of excess skin surface by abrasion (2) polishing of abraded skin surface to smoothen it, and (3) re-building of abraded skin by enhancement of collagen synthesis and boosting of other skin fibers. In addition, the inclusion of an anti-inflammatory agent to soothe the skin, blood microcirculation enhancement agent to bring additional blood carrying skin nutrients and oxygen (to further promote skin rebuilding), and an emollient to seal the skin from excessive moisture loss from freshly exposed skin surface would also be highly beneficial.

It is also clear from the above prior art citations that no such comprehensive skin treatment systems currently exist, although their usefulness and consumer desirability is obvious to those who are versed in this art.

The present invention provides a novel solution to this problem by using a complementary three-step treatment process that does not require any expensive machine or apparatus, unsafe or harsh chemical, or services of a trained professional or physician. This three-step treatment can be self-administered easily at home by consumer. This three-step dermabrasion system of the present invention constitutes the following, (1) Dermal Resurfacing with an adhesive gel, (2) Dermal Polishing with a polishing composition, and (3) Dermal Regeneration with a collagen-building and cell-proliferative composition with the inclusion of anti-inflammatory agents and emollients.

SUMMARY OF INVENTION

Dermabrasion provides treatment for skin conditions such as acne scars, wound scars, disfigurements of skin from diseases such as small pox, and other topical disfigurements. The present invention provides a comprehensive solution to this problem by a three-step treatment process that does not require any expensive machine, unsafe or harsh chemical, or services of trained professionals. This three-step treatment, which can be self-administered easily at home by consumer, constitutes the following (1) Dermal Resurfacing with an adhesive gel, (2) Dermal Polishing with a polishing composition, and (3) Dermal Regeneration with a collagen-building and cell-proliferative composition with the inclusion of anti-inflammatory agents and emollients.

DETAILED DESCRIPTION

The present invention provides a complementary three-step dermabrasion system that provides treatment for skin conditions such as acne scars, wound scars, disfigurements of skin from diseases such as small pox, and other dermal tissue disfigurements, which constitutes the following, (1) Dermal Resurfacing with an adhesive composition, (2) Dermal Polishing with a polishing composition, and (3) Dermal Regeneration with a collagen-rebuilding and cell-proliferative composition.

Dermal Resurfacing Composition: The dermal resurfacing composition is an adhesive-based system that removes skin one to two layers at a time. This provides a controlled removal of unwanted or excessive skin at an acne or wound scar site. This is much superior to tape stripping method, as the adhesive composition can be applied directly on the area of affliction without affecting adjacent areas of normal skin. This eliminates unnecessary removal of skin area immediately adjacent to the scar tissue area to be removed.

The adhesive compositions of the present invention have been disclosed by the present inventor, in their basic form, in U.S. patent application Ser. No. 10/249,012 (filed Mar. 10, 2003) and U.S. patent application Ser. No. 10/248,925 (filed Mar. 3, 2003). However, these patent applications have disclosed certain hair removal (depilatory) compositions, which are different in their utility from the intended purpose of the present invention. While in depilatory applications it is important to increase the hair adhesiveness and simultaneously decrease the skin adhesiveness of a composition, for dermal resurfacing applications the hair adhesiveness is decreased and skin adhesiveness is increased. Surprisingly, it has been possible to modify the adhesive properties of hair removal compositions for the intended purpose of increasing their skin adhesiveness to act as skin stripping agents. Accordingly, the dermal resurfacing compositions of the present invention constitute the following, (i) At least one skin binding composition, and(ii) At least one protective coating composition, and (iii) At least one liquid binder composition that binds with the ingredients of the compositions in (i) and (ii).

Moreover, these compositions do not require any preheating or microwave step prior to their application. Additionally, they can be either opaque or transparent in appearance.

The skin binding composition can be selected from a number of natural or synthetic adhesives, of which a wide selection of rosin, rosinates, and polymers can be utilized either alone or in combination. The examples include, but not limited to Wood Rosin, Glyceryl Rosinate, Glyceryl Hydrogenated Rosinate, Polyethylene Glycol Rosinate, Polyethylene Glycol Hydrogenated Rosinate, Pentaerythritol Rosinate, Abietyl alcohol, Abietyl esters, Pentaerythritol Hydrogenated Rosinate, Polyvinyl Alcohol, Polyvinyl Acetate, Polyvinyl Esters, PVP, PVP/PVA Copolymers, Dimerized Rosin, Esters of Dimerized Rosin, Modified Wood Rosin, Esters of Modified Wood Rosin, Polyol Ester Rosinate, Polyterpene Resins, Esters of Hydrogenated Modified Rosin; (Hydrogenated Rosins covers both fully and partially hydrogenated forms), Polyethylene, Polypropylene, Polystyrene, Polyisobutylenes, EVA Resins, Block Copolymers, Polyvinyl Ethers, Polyacrylics, Polyvinyl butyral, Polyamides, Aromatic Hydrocarbon Resin, Cellulose Acetate, Ethyl Cellulose, Cellulose Acetate Butyrate, Ethyl Hydroxyethylcellulose, Nitrocellulose, Alkyl Resins, Rosin Ester Resins, Hydrocarbon waxes, Natural Waxes, Shellac, Natural Rubber, Styrene-Butadiene Rubber, Nitrile Rubber, Butyl Rubber, Polychloroprene Rubber, and Chlorinated Rubber.

The compositions of the present invention also include at least one protective skin coating composition. The purpose of such compositions is to provide slip during the pulling of the fabric, plastic, or paper for skin removal, thus protecting any damage to the lower layers of skin during skin removal process. This makes the removal of the composition from the skin surface easier, thus eliminating or significantly reducing any damage to the inner layers of skin that can cause the skin irritation or infection. The protective skin coating agent can be selected from, but not limited to, natural oils, natural butters, natural waxes, synthetic oils, synthetic waxes, silicone oils, silicone waxes, silicone elastomers, Silicone Rosinates, Alkoxylated Silicone Rosinates, organic siloxanes, and their cross polymer (e.g., dimethicone, dimethicone copolyol, cetyl dimethicone copolymer, cetyl dimethicone, stearyl dimethicone, stearoxydimethicone, behenoxydimethicone, alkyl methicone, amodimethicone, dimethicone alkyl betaine, cyclomethicone, polydimethylsiloxane, diphenyldimethyl polysiloxane, silicone elastomers, cyclomethicone and dimethicone crosspolymer, Jeesilc 6056, Dow Corning 2501, modified celluloses, hydroxyethyl cellulose, ethyl cellulose, carboxymethyl cellulose, ethyl hydroxyethyl cellulose, xanthan gum, gellan gum, guar gum, cationic polymers, Aristoflex AVC (Ammonium Acryloyldimethyltaurate/VP Copolymer), Structure Plus and Structure XL (Acrylates/Aminoacrylates/c10–30 Alkyl PEG-20 Itaconate Copolymer), Carbomer, Carbopol ETD 2020 (Acrylate C10–30 Alkyl Acrylate Crosspolymer), Rheocin (trihydroxystearin), Hydramol PGDS (PEG-90 Diisostearate), C24–28 Alkyl Dimethicone, Behenyl alcohol, quaternary ammonium compounds, sugar derivatives, and combinations thereof.

The third component of the present invention is the inclusion of at least one liquid binder composition that binds with all other ingredients of the skin binding composition. The most important feature is that such liquid binder composition provides the skin binding composition as a mobile, easy to pour and spreadable liquid form that does not require any pre-heating or microwave step prior to its application on skin. Moreover, such liquid binder does not absorb into fabric, paper, or plastic piece on which the skin binding composition may be in contact during the skin removal process. Moreover, the liquid binder composition does not evaporate; thus causing the crystallization of its components that can cause the loss of skin removal power of such compositions.

The preferred liquid binder agent or composition can be selected from, but not limited to, natural oils (such as almond oil, castor oil, linseed oil, sunflower seed oil, mango oil, coconut oil, corn oil, vegetable oil, sesame seed oil, jojoba oil, pistachio nut oil, macadamia nut oil, and such), natural butters (such as mango butter, coco butter, almond butter, shea butter, aloe butter, sal butter, kokum butter, butters made from hydrogenated natural oils, and such), polyethylene glycol, polypropylene glycol, polybutylene glycol, methylpropanediol, various carbowax derivatives, propylene glycol, butylene glycol, hexylene glycol, ethoxydiglycol pyrrolidone, N-Methyl pyrrolidone, DMSO, and combinations thereof.

The skin removal cosmetic compositions of the present invention are suitable for site-specific applications with the following attributes: (1) A pre-heating or microwave step is not necessary, (2) Controlled skin removal is achieved per single application on a specific site or area, (3) Essentially no skin irritation is experienced, (4) Bond to skin preferentially, (5) Provide lubricity and emolliency to skin, (6) Can be applied either directly on the skin followed by placement of a piece of precut fabric, plastic or paper over the area of application. Alternatively, dispensing applicators can also be used that can be filled for delivery at the specific site where skin stripping is desired. (7) Require minimal clean-up with common make-up removal compositions, and (8) Additional skin beneficial ingredients, such as anti-irritants, topical pain relief agents, antioxidants, skin soothing agents, skin cooling agents, emollients, moisturizers, topical anesthetics, colorants, botanical extracts, fragrances, and such can be included.

Dermal Polishing Composition. For efficacious smoothing of skin after resurfacing step a polishing step is required.

The polishing composition is comprised of the following: (i)At least one solid abrasive material suitable for skin polishing, and (ii) At least one skin softening composition, and (iii) A carrier base or delivery system composition.

For skin polishing a solid material with certain hardness value is required. The examples of such materials include, but not limited to silica, fumed silica, silica gels, alumina, zirconia, corundum, metal shavings, seeds and seed fragments, titanium dioxide, zinc oxide, jojoba beads, wax beads, polyethylene beads, ion exchange resin beads, clays, montmorillonite, bentonite, zeolites, luffa particles, starch granules, and such.

A number of hydroxy acids (AHA) and their derivatives are well known for their skin exfoliation benefits. Several new AHA derivatives have recently been disclosed by the present inventor for their antiaging and anti-wrinkle benefits (U.S. patent application Ser. No. 10/290,933, filed Nov. 7, 2002). In the course of present invention it has surprisingly been found that AHA and their derivatives also provide skin softening benefits in a cosmetic composition. Accordingly, the compositions of the present invention can contain one or more of such AHA and their derivatives as skin softening agents, for example lactic acid, glycolic acid, malic acid, mandelic acid, hydroxy citric acid, tartaric acid, allantoin lactate, allantoin glycolate, allantoin mandelate, allantoin malate, allantoin ascorbate, allantoin phytate, allantoin citrate, allantoin hydroxy citrate, allantoin aleurate, allantoin salicylate, allantoin hyaluronate, glucosamine lactate, glucosamine glycolate, glucosamine malate, glucosamine mandelate, glucosamine ascorbate, glucosamine phytate, glucosamine citrate, glucosamine hydroxy citrate, glucosamine aleurate, glucosamine salicylate, glucosamine hyaluronate, creatine lactate, creatine glycolate, creatine malate, creatine mandelate, creatine ascorbate, creatine phytate, creatine citrate, creatine hydroxy citrate, creatine aleurate, creatine salicylate, creatine hyaluronate, niacinamide lactate, niacinamide glycolate, niacinamide malate, niacinamide mandelate, niacinamide ascorbate, niacinamide phytate, niacinamide citrate, niacinamide hydroxy citrate, niacinamide aleurate, niacinamide salicylate, niacinamide hyaluronate, Inositol Niacinate Ascorbate, pyridoxine lactate, pyridoxine glycolate, pyridoxine malate, pyridoxine mandelate, pyridoxine ascorbate, pyridoxine phytate, pyridoxine citrate, pyridoxine hydroxy citrate, pyridoxine aleurate, pyridoxine salicylate, pyridoxine hyaluronate, chitosan lactate, chitosan glycolate, chitosan malate, chitosan mandelate, chitosan ascorbate, chitosan phytate, chitosan citrate, chitosan hydroxy citrate, chitosan aleurate, chitosan salicylate, chitosan hyaluronate, and combinations thereof.

Although dermabrasion compositions that contain abrasive particulates in a cream or lotion base have been disclosed in the prior art, for example U.S. Patent Application 20030049291 (Cheski), such compositions still require the use of a special tool or device for their application on skin. Buffing compositions, for example U.S. Patent Application 20010046506 (Rhoades) and U.S. Pat. No. 6,290,976 (Messenger) do not provide a complete treatment system, including skin softening via promotion of skin exfoliation at mesodermal layers, to cause easier removal of skin during such buffing operations. Prior art scrubbing cleanser disclosures, for example U.S. Pat. No. 5,891,449 (Daniel et al.), U.S. Pat. No. 5,679,877 (Erilli et al.), U.S. Pat. No. 5,753,245 (Fowler et al.), U.S. Pat. No. 4,992,476 (Geria et al.), U.S. Pat. No. 5,360,824 (Barker), and U.S. Pat. No. 4,284,533 (Imamura et al.) are more suitable for body cleansing applications with removal of dead skin cells.

Dermal Regeneration Composition. For efficacious regeneration of skin from topical treatments, it would thus be advantageous to include the following provisions in a single composition:(1) Boosting of collagen synthesis, (2) Control of inflammation, (3) Enhancement of blood microcirculation, and (4) Protection of freshly exposed skin from excessive moisture loss.

The composition to promote collagen and elastin in the skin can be selected from, but not limited to, Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, Potentilla erecta extract, Polyphenols, Grapeseed extract, Pycnogenol (Pine Bark extract), and combinations thereof. The quantities of such compositions can be safe and effective amounts as needed, and not limited to any specific limits.

The compositions for the control of inflammation can be selected from, but not limited to, a number of already well known anti-oxidants with COX-1, COX-2, and LOX inhibiting action, and also other anti-inflammatory agents. A number of these compositions are also well known for their collagen synthesis boosting effects as well. Examples of anti-inflammatory agents include, but not limited to Ascorbic acid, Ascorbic acid derivatives, Glucosamine ascorbate, Arginine ascorbate, Lysine ascorbate, Glutathione ascorbate, Nicotinamide ascorbate, Niacin ascorbate, Allantoin ascorbate, Creatine ascorbate, Creatinine ascorbate, Chondroitin ascorbate, Chitosan ascorbate, Inositol Niacinate Ascorbate, DNA Ascorbate, Carnosine ascorbate, Vitamin E, various Vitamin E derivatives, Tocotrienol, Rutin, Quercetin, Hesperedin (*Citrus sinensis*), Diosmin (*Citrus sinensis*), Mangiferin (*Mangifera indica*), Mangostin (*Garcinia mangostana*), Cyanidin (*Vaccinium myrtillus*), Astaxanthin (*Haematococcus algae*), Lutein (*Tagetes patula*), Lycopene (*Lycopersicum esculentum*), Resveratrol (*Polygonum cuspidatum*), Tetrahydrocurcumin (*Curcuma longa*), Rosmarinic acid (*Rosmarinus officinalis*), Hypericin (*Hypericum perforatum*), Ellagic acid (*Punica granatum*), Chlorogenic acid (*Vaccinium vulgaris*), Oleuropein (*Olea europaea*), α-Lipoic acid, Niacinamide lipoate, Glutathione, Andrographolide (*Andrographis paniculata*), Carnosine, Niacinamide, Potentilla erecta extract, Polyphenols, Grapeseed extract, Pycnogenol (Pine Bark extract), pyridoxine, Horse Chestnut Extract (*Aesculus hippocastanum* extract)), Esculin, Escin, Yohimbine, Capsicum Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), Boswellia Extract (*Boswellia serrata*), Ginger Root Extract (*Zingiber Officinalis*), Piperine, Vitamin K, Melilot (*Melilotus officinalis* extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis-Vinifera*) leaves, apigenin, phytosan, luteolin, and combinations thereof.

The enhancement of blood micro-circulation provides extra oxygen for faster metabolism of any excess sebum oil in the upper layers of skin. This enhanced blood flow also removes any irritation and inflammation causing materials from the immediate vicinity of afflicted area. Additionally, increased blood circulation in the micro-capillaries can also stimulate faster cell turnover, further resulting in enhanced replacement of skin cells that have been removed by resurfacing step. The amount of at least one composition to improve blood micro-circulation can be from 0.0001% to 10%, preferably from about 0.01% to 5%, and most preferably from about 0.1% to 1%. The blood microcirculation improvement composition can be selected from Horse Chestnut Extract (*Aesculus hippocastanum* extract)), Esculin, Escin, Yohimbine, Capsicum Oleoresin, Capsaicin, Niacin, Niacin Esters, Methyl Nicotinate, Benzyl Nicotinate, Ruscogenins (Butchers Broom extract; *Ruscus aculeatus* extract), Diosgenin (*Trigonella foenumgraecum*, Fenugreek), Emblica extract (*Phyllanthus emblica* extract), Asiaticoside (*Centella asiatica* extract), *Boswellia* Extract (*Boswellia serrata*), Ginger Root Extract (*Zingiber Officinalis*), Piperine, Vitamin K, Melilot (*Melilotus officinalis*extract), Glycyrrhetinic acid, Ursolic acid, Sericoside (*Terminalia sericea* extract), Darutoside (*Siegesbeckia orientalis* extract), Amni visnaga extract, extract of Red Vine (*Vitis Vinifera*) leaves, apigenin, phytosan, luteolin, and combinations thereof.

The compositions for the protection of freshly exposed skin from excessive moisture loss include a large number of emollients and moisturizers that includes, but not limited to glycerin, vegetable oils, mineral oil, natural butters, paraffin, petrolatum, organosilicones, organic siloxanes, and their cross polymer (e.g., dimethicone, dimethicone copolyol, cetyl dimethicone copolymer, cetyl dimethicone, stearyl dimethicone, stearoxydimethicone, behenoxydimethicone, alkyl methicone, amodimethicone, dimethicone alkyl betaine, cyclomethicone, polydimethyl-siloxane, diphenyldimethyl polysiloxane, silicone elas-tomers, cyclomethicone and dimethicone crosspolymer, ethylene glycol, propylene glycol, butylene glycol, hexylene glycol, pyrrolidone, N-methyl pyrrolidone, dimethyl sulfoxide, dimethyl sulfone, polyethylene glycol, polypropylene glycol, methylpropanediol, Allantoin, dimethicone, urea, calamine, kaolin, zinc acetate, zinc carbonate, and such.

The cosmetically acceptable delivery system or a carrier base of the present invention can be selected in the form of a lotion, cream, gel, spray, thin liquid, body splash, mask, serum, solid cosmetic stick, balm, salve, collodion, impregnated patch, impregnated strip, skin surface implant, and any other such cosmetically or pharmaceutically acceptable topical delivery forms. Cosmetically or pharmaceutically acceptable delivery system can also be traditional water and oil emulsions, suspensions, colloids, microemulsions, clear solutions, suspensions of nanoparticles, emulsions of nanoparticles, powders, or anhydrous compositions. Cosmetically or pharmaceutically acceptable delivery system or carrier base can optionally include additional skin beneficial ingredients selected from skin cleansers, surfactants (cationic, anionic, non-ionic, amphoteric, and zwitterionic), skin and hair conditioning agents, vitamins, hormones, minerals, plant extracts, anti-inflammatory agents, concentrates of plant extracts, emollients, moisturizers, skin protectants, humectants, silicones, skin soothing ingredients, analgesics, skin penetration enhancers, solubilizers, moisturizers, emollients, anesthetics, colorants, perfumes, preservatives, seeds, broken seed nut shells, silica, clays, beads, and luffa particles.

EXAMPLES

The examples are for illustrative purposes only and do not reflect any limitations to the process or practice of this invention. All quantities are in weight percentages.

Example 1

Dermal Resurfacing Gel Composition 1. (1) PPG-20 29.7 (2) Hydrocarbon Resin (Arizona Chemical Sylvares 520) 69.0 (3) Mango butter 0.5 (4) BHT 0.1 (5) Cocoa butter 0.2 (6) Shea butter 0.5. Procedure. Mix all ingredients and heat at 75 to 85° C. till a clear liquid is obtained. Cool to room temperature. A clear mobile soft gel is obtained.

Example 2

Dermal Resurfacing Gel Composition 2. (1) Glyceryl Hydrogenated Rosinate (melting point 80° C.) 25.8 (2) Modified Rosin Ester (melting point 25° C.) 68.0 (3) Mango butter (and) shea butter (and) sal butter (and) grape seed oil (and) kiwi seed oil 4.0 (4) Tetradibutyl pentaerythrityl Hydroxyhydrocinnamate 0.2 (5) Siliconyl Beeswax 2.0. Procedure. Mix all components and heat at 70 to 75° C. to a clear liquid. Cool to room temperature. A transparent, light amber non-mobile gel is obtained.

Example 3

Dermal Resurfacing Gel Composition 3. (1) Abietyl Alcohol 70.0 (2) Modified Rosin Ester 25.8 (3) Mango butter (and) shea butter (and) sal butter (and) grape seed oil (and) kiwi seed oil 4.0 (4) Tetradibutyl pentaerythrityl Hydroxyhydrocinnamate 0.2 (5). Procedure. Mix all components and heat at 70 to 75° C. to a clear liquid. Cool to room temperature. A transparent mobile gel is obtained.

Example 4

Dermal Polishing Gel Composition. (1) PEG-6 50.5 (2) Ammonium Acryloyldimethyltaurate/VP Copolymer 0.8 (3) Glycerin 5.0 (4) Deionized Water 20.0 (5) Vitamin E Acetate 0.1 (6) Geogard 221 (Preservative) 0.5 (7) Cyclomethicone and dimethicone crosspolymer 10.0 (8) Actiplex (Plant Extracts Blend) 0.1 (9) Alumina powder, (40/60 mesh) 8.0. (10) Niacinamide Lactate 5.0. Procedure. Mix ingredients 2, 3 and 4 together until a clear gel is formed. Add all other ingredients to the clear gel and mix to produce a main batch. A polishing gel is obtained.

Example 5

Dermal Polishing Mask Composition. (1) Paraffin wax 25.0 (2) Cetyl alcohol 1.0 (3) Propyl paraben 0.1 (4) Methyl paraben 0.2 (5) GMS-SE4.0 (6) Stearic acid 3.0 (7) Emulsifying wax 5.0 (8) Deionized water 43.9 (9) Vitamin K 0.3 (10) Pyridoxine Salicylate 0.5 (11) Corn starch 5 (12) Polydimethylsiloxane 2.0 (13) Polyethylene beads 10.0. Procedure: All ingredients are mixed and heated at 60 to 70° C. The mixture is cooled to room temperature. A thick paste is obtained.

Example 6

Dermal Polishing Lotion Composition. (1) Deionized water 77.749 (2) Carbomer 1.5 (3) Grapeseed Extract 0.0001 (4) Vitamin C 0.0002 (5) Aloe Vera 0.0007 (6) Preservative 0.7 (7) Chitosan Malate 0.1 (8) Chitosan Lactate 0.1 (9) Chitosan Glycolate 0.1 (10) Polysorbate-20 0.2 (11) Fragrance 0.05 (12) Alumina 7.0 (13) Disodium Lauryl sulfosuccinate 7.0 (14) Corn starch 5.0. Procedure. Mix (1) and (2) till a gel is formed. Add all other ingredients. A cream-like composition is obtained.

Example 7

Dermal Regenerative Cream Composition. (1) Deionized Water 66.0 (2) Glycerin 2.0 (3)Aloe Vera 1.2 (4) Acrylates/C10–30 Alkyl Acrylate Crosspolymer 0.2 (5) Carbomer 0.2 (6) Sodium Hydroxide 0.2 (7) Sodium Stearyl Phthalamate 1.0 (8) EDTA 0.2 (9) Dimethicone 5.0 (10) Alkyl Benzoate 5.0 (11) GMS-SE 0.5 (12) Silicone elastomers 5.0 (13) Cetyl Alcohol 2.0 (14) Phenoxyethanol 0.7 (15) Dehydroacetic acid 0.3 (16) Cetyl Dimethicone Copolyol 5.0 (17) Vitamin E Acetate 0.2 (18) Centella Asiatica Extract 0.5 (19) Tetrahydrocurcumin 0.2 (20) Escin 0.5 (21) Boswellia Serrata Extract 0.5 (22) Inositol Niacinate Ascorbate 0.5 (23) Vitamin K-1 0.1 (24) N-Acetyl-Glucosamine 2.5 (25) Hyaluronic Acid 0.1 (26) Carnosine 0.4. Procedure: Mix all ingredients and heat at 60 to 70° C. Homogenize, then cool to room temperature. The pH is adjusted to 6.5 to 7.5. An off-white cream is obtained.

Example 8

Dermal Polishing Cleanser Cream Composition. (1) PEG-6 34.0 (2) Glycerin 4.0 (3) Vitamin A Palmitate 0.1 (4) Vitamin E Acetate 0.1 (5) Dehydroacetic acid (and) Benzyl alcohol 0.7 (6) Zeolite, 4A 31.95 (7) Disodium Lauryl Sulfosuccinate 8.5 (8) Sodium Cocoyl Isethionate 14.0 (9) Mango Seed Oil 0.5 (10) Aloe Butter 0.5 (11) Shea Butter 0.5 (12) Walnut shells (crushed 40/60 mesh) 4.0 (13) Copper ATP 0.1 (14) Glutathione 0.05 (15) Fragrance 1.0. Procedure. Mix all ingredients at 35 to 50° C. Cool to room temperature. A cream-like composition is obtained with excellent skin softening, abrasion, cleansing, foaming, self-heating, and moisturization benefits.

Example 9

Procedure for the Application of Three-step Dermabrasion System.

Step 1. Dermal Resurfacing Treatment. The dermal resurfacing composition is applied at the site of skin removal with a spatula or swab. A piece of fabric, plastic, or paper is placed over the area of product application and firmly pressed with fingers. It is then pulled off with fingers in a fast motion. The piece of fabric, plastic, or paper thus removed contains the layers of cells removed. It can be observed with a microscope, if so desired. Step 2. Dermal Polishing Treatment. The dermal polishing composition is applied at the site of skin polishing and massaged with fingers or a piece of cheese cloth in a circular motion. It is then rinsed off with water. Step 3. Dermal Regeneration Treatment. The dermal regeneration composition is applied to the skin site and massaged with fingers till absorbed.

I claim:

1. A three-step cosmetic dermabrasion treatment system or method comprising; (i) A non-acidic dermal resurfacing composition, and having a softening point of less than 80C, and (ii) A dermal polishing composition, and (iii) A dermal regenerating composition, and wherein (i), (ii), and (iii) are sequentially applied to skin.

2. A cosmetic Dermabrasion treatment method according to claim 1, wherein said treatment is for skin antiaging, including wrinkles.

3. A cosmetic Dermabrasion treatment method according to claim 1, wherein said treatment is for acne.

4. A cosmetic Dermabrasion treatment method according to claim 1, wherein said treatment is for correcting minor skin imperfections.

5. A dermabrasion treatment method according to claim 1, wherein dermal resurfacing composition is a non-acidic adhesive composition, comprising; (i) At least one skin binding composition, and (ii) At least one skin coating composition, and (iii) At least one liquid binder composition that binds with the ingredients of the compositions in (i) and (ii).

6. A dermabrasion treatment method according to claim 1, wherein dermal polishing composition comprising; (i) At least one solid material for skin polishing, and (ii) At least one skin softening composition, and (iii) A carrier base.

7. A dermabrasion treatment method according to claim 1, wherein dermal regenerating composition comprising; (i) At least one collagen boosting composition, and (ii) At least one anti-inflammatory composition, and (iii) At least one blood microcirculation enhancing composition, and (iv) At least one emollient composition, and (v) A carrier base.

8. A dermabrasion treatment method according to claim 1, wherein components (i), and/or (ii), and/or (iii) additionally contains at least one topical anesthetic selected from benzocaine, dibucaine, dyclonine, lidocaine, pramoxine, tetracaine, ephedrine, epinephrine, phenylephrine, and their various salt derivatives.

9. A dermabrasion treatment method according to claim 5, wherein said method requires temperatures less than 80C.

10. A dermabrasion treatment method according to claim 5, wherein skin binding composition is an aromatic hydrocarbon resin having a softening point of less than 80C.

11. A composition according to claim 6, wherein a carrier base is selected from a lotion, cream, gel, spray, thin liquid, mask, serum, solid cosmetic stick, balm, salve, collodion, impregnated patch, traditional water and oil emulsion, suspension, colloid, microemulsion, clear solution, suspension of nanoparticles, emulsion of nanoparUcles, powder, or anhydrous composition.

12. A composition according to claim 7, wherein a carrier base is selected from a lotion, cream, gel, spray, roll-on, glide-on, thin liquid, mask, serum, solid cosmetic stick, balm, salve, collodion, impregnated patch, impregnated strip, traditional water and oil emulsion, suspension, colloid, microemulsion, clear solution, suspension of nanoparticles, emulsion of nanoparticles, powder, or anhydrous composition.

* * * * *